United States Patent [19]

Kershner

[11] Patent Number: 5,167,618
[45] Date of Patent: Dec. 1, 1992

[54] CAPSULOTOMY FORCEPS

[76] Inventor: Robert M. Kershner, 1925 W. Orange Grove Rd. #303, Tucson, Ariz. 85704

[21] Appl. No.: 659,979

[22] Filed: Feb. 22, 1991

[51] Int. Cl.$^5$ .............................................. A61B 17/20
[52] U.S. Cl. ..................................... 604/22; 606/205; 606/210
[58] Field of Search ...................... 294/99.1, 99.2, 100; 606/205-209, 210-211; 604/264, 272, 239

[56] References Cited

U.S. PATENT DOCUMENTS

| 740,549 | 10/1903 | Gilbert | 294/99.2 |
| 5,047,049 | 9/1991 | Sazai | 606/205 |

FOREIGN PATENT DOCUMENTS 932982  7/1963  United Kingdom ................ 606/207

OTHER PUBLICATIONS

Surgical Instruments, Sklar Product, J. Sklar Mfg. Co., Inc. Long Island City N.Y. 18th edition 1973.

Primary Examiner—C. Fred Rosenbaum
Assistant Examiner—Manuel Mendez
Attorney, Agent, or Firm—Cahill, Sutton & Thomas

[57] ABSTRACT

Forceps used for performing a capsulotomy have relatively movable blades, the distal ends of which carry downwardly-projecting, sharp cystotomes. A first portion of each blade adjacent its distal end extends in a generally horizontal direction and is joined to a second portion extending upwardly at an acute angle with respect to the first portion. The forceps blades may either be connected to a handle or a syringe. In the latter case, one of the blades has a fluid flow passage therein in communication with the interior of the syringe.

2 Claims, 1 Drawing Sheet

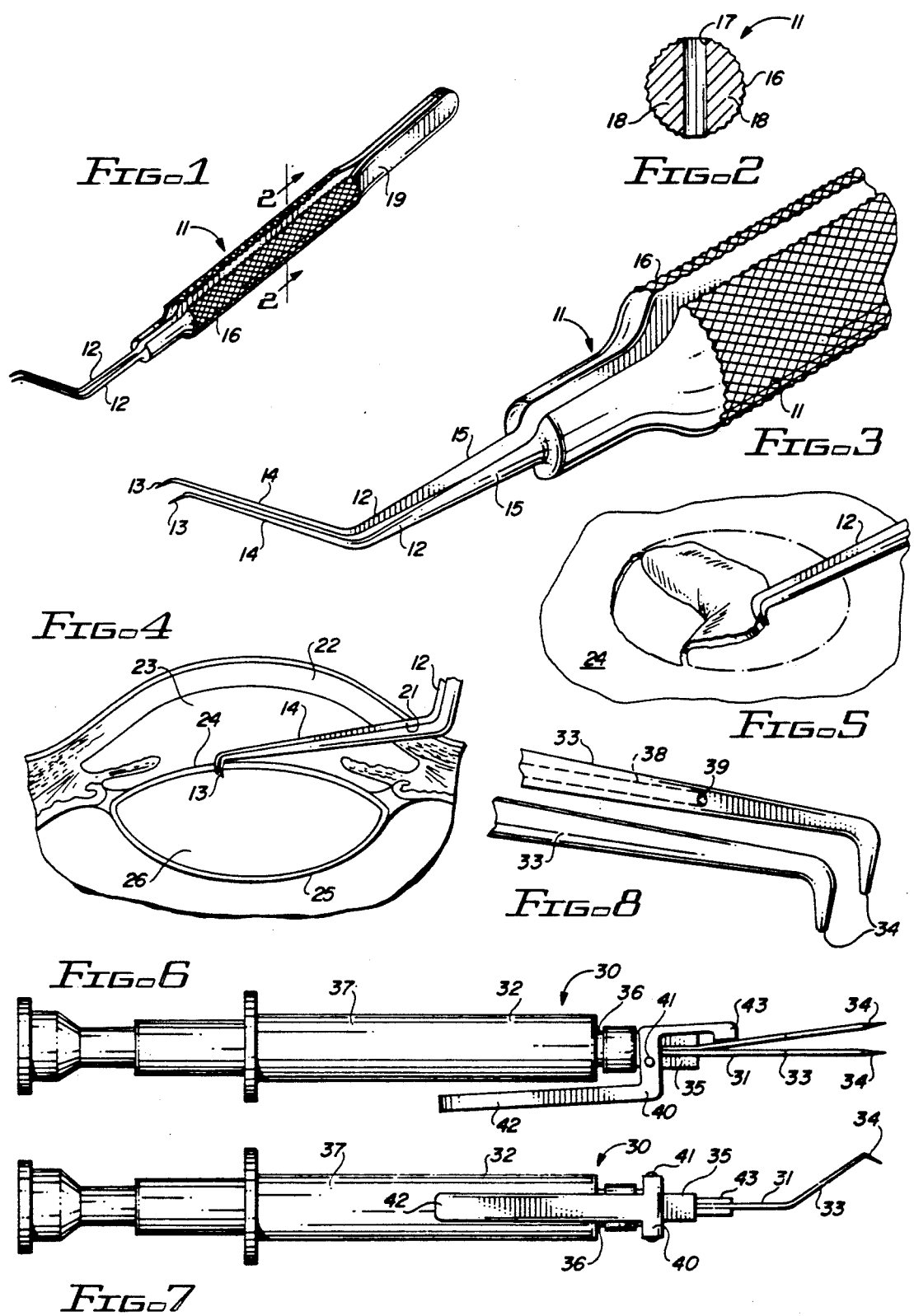

CAPSULOTOMY FORCEPS

TECHNICAL FIELD

This invention is concerned with surgical removal of cataracts and provides an instrument which combines the functions of a cystotome and forceps for performing a continuous tear capsulotomy which is known as a "capsulorhexis".

BACKGROUND ART

Opacification of the crystalline lens of the eye produces what is commonly referred to as a cataract. Restoration of sight is usually effected by surgical removal of the affected lens and possible replacement with an artificial intraocular lens.

In extracapsular cataract extraction, a small incision is made in a peripheral portion of the cornea or sclera. A cystotome instrument is inserted through the incision and employed to cut open the anterior wall of the capsule containing the lens. This procedure is referred to as a capsulotomy. The lens is then removed through the openings in the anterior wall and the cornea.

In a cataract extraction technique known as phacoemulsification, the lens is emulsified with an ultrasonic probe and sucked out of the eye through a passage in the probe.

These cataract extraction techniques are well known and are described and illustrated, for example, at Pages 84-91 in Cataracts by Julius Schulman, M.D., published in 1984 by Simon & Schuster, Inc. The capsulotomy there described employs a needle cystotome to make numerous cuts, resembling beer can openings, in the anterior wall of the capsule. The resulting rough edge at the opening in the anterior wall can sometimes interfere with phacoemulsification and aspiration of the lens.

U.S. Pat. No. 4,708,138, granted Nov. 24, 1987, to B. B. Pazandak for "Rotating Surgical Cutting Knife" discloses an instrument with a movable cutting blade intended to produce a smoother anterior capsulotomy.

A more recent approach to capsulotomy involves creating a continuous tear of the anterior wall to produce a smooth-edged round opening. The continuous tear capsulotomy is known as "capsulorhexis". Such a capsulotomy facilitates removal of the old lens and also facilitates in-the-bag implantation of an intraocular lens.

The present invention provides a forceps instrument which is particularly useful in performing the capsulorhexis.

United Kingdom Patent No. 113,482, dated Feb. 21, 1918, discloses "New and Improved Eye Forceps" for cataract removal. The construction of the forceps there disclosed provides for removal of not only the lens but also the entire capsule containing the lens. This is a much more traumatic operation than extracapsular extraction.

U.S. Pat. No. 3,834,021, granted Sep. 10, 1974, to R. W. White, et. al. for "Precision Instrument System" discloses a scissors-type surgical instrument which can be manipulated by one hand. The instrument would appear to have no usefulness in eye surgery.

DISCLOSURE OF THE INVENTION

The forceps of this invention has two blades which are normally spaced a short distance apart, but the blades are relatively movable toward each other. Carried at the distal ends of the two blades are depending, sharp, cystotome tips. The tips are capable of penetrating the anterior wall of the lens capsule when pressed against that wall. A first portion of each blade extends generally horizontally away from the tips and is joined to a second portion disposed at an acute angle to the first portion. The blades are either carried by a handle or on a syringe. In the latter configuration, one blade has a fluid passage therethrough in communication with the interior of the syringe. The forceps further include means for moving the blades relative to each other to clamp a portion of the anterior wall between the tips of the blades so that further movement of the blades can cause tearing of the anterior wall.

BRIEF DESCRIPTION OF THE DRAWINGS

The invention is described in greater detail hereinafter by reference to the accompanying drawings, wherein:

FIG. 1 is an elevational view of a capsulotomy forceps instrument constructed in accordance with this invention;

FIG. 2 is a sectional view through the instrument taken as indicated by lines 2—2 in FIG. 1;

FIG. 3 is an enlarged view of the blades of the instrument;

FIG. 4 is a fragmentary, sectional view through a human eye illustrating use of the instrument;

FIG. 5 is a perspective view illustrating the manner in which the instrument is used to tear the anterior wall of a lens capsule;

FIG. 6 is a top view of an instrument constructed in accordance with this invention and employing a syringe for introducing fluid into the eye;

FIG. 7 is a side view of the instrument shown in FIG. 6; and

FIG. 8 is an enlarged view of the forceps blades of the instrument shown in FIGS. 6 and 7.

BEST MODES FOR CARRYING OUT THE INVENTION

One version of the capsulotomy forceps instrument of this invention is illustrated in FIGS. 1-3 and is designated generally by the reference numeral 11. This instrument is characterized by possessing a pair of elongated blades, or jaws, 12. The distal ends of the blades 12 carry sharp, triangular-shaped, depending cystotome tips 13.

Referring particularly to FIG. 3, each blade 12 has a first portion 14 extending away from the tip 13 in a generally horizontal direction. Joined to the end of the first portion of each blade is a second portion 15 which extends upwardly from the first portion at an acute angle, preferably in the 40° to 60° range and most preferably at approximately 50°. The opposite ends of the second portions of the blade are joined to a handle 16.

Handle 16 preferably has a cylindrical configuration with a longitudinal slot 17 therein. The handle thus possesses two identical spaced sections 18 which are connected, respectively, to the two blades 12. The ends of the handle portions 18 opposite the blades 12 are joined together with a thin, spatula-shaped hand rest 19. The surface of handle 16 is preferably knurled for non-slip gripping between the thumb and forefingers of the surgeon.

In this version of the forceps 11, the handle 16 serves as the means for effecting relative movement of the blades 12 to bring together and separate the cystotome tips 13. The instrument preferably is constructed in such a manner that when it is at rest, the cystotome tips 13 are separated a small distance, say 2–3 mm. By grasping and squeezing the handle 16, the surgeon can move the handle sections 18 together to bring the cystotome tips into contact with each other.

The entire instrument 11 is preferably fabricated from a durable, sterilizable material such as titanium.

The manner in which forceps instrument 11 is used is illustrated in FIGS. 4 and 5. A small incision 21 is made in a peripheral region of the cornea 22. The surgeon grasps the handle 16 to close the blades 12 and insert the first portions 14 of the blades through the incision into the anterior chamber 23 of the eye. The surgeon next opens the blades 12 approximately 1–1.5 mm and presses one or both cystotome tips 13 into and through the anterior wall 24 of the capsule 25 containing the lens 26 (FIG. 4). The blades 12 are closed to grip the anterior wall between tips 13. Rotation of handle 16 tears the gripped anterior wall in the manner illustrated in FIG. 5. With repetition of this sequence, the surgeon is able to separate a nearly circular flap from the anterior wall.

It has been determined that this capsulorhexis can be performed with maximum finger tip control and less hand movement if the first portions 14 of the blades 12 have lengths of approximately 8 mm. Further, to minimize wound gape, at least the first portions 14 of the blades 12 have round cross sections and are very thin, less than 1 mm in diameter.

Another version of the capsulotomy forceps instrument of the invention is illustrated in FIGS. 6–8 and is identified generally by reference numeral 30. Actually, this instrument is a combination of a forceps 31 and a syringe 32. The forceps 31 comprises a pair of blades 33 which outwardly are substantially the same as the blades shown in FIG. 3 and described above. As with that version, the blades have cystotome tips 34 on the distal ends thereof. The proximal ends of the blades 33 are mounted in a hub 35 adapted to fit over the nozzle 36 of the syringe barrel 37. One of the blades 33 of the forceps 31 has a passage 38 therein (see FIG. 8) having a discharge opening 39 therefrom near the distal end of the blade. The passage 38 is in communication with the interior of syringe 32.

The forceps 31 is manipulated by a lever 40 pivotally mounted at 41 to the forceps hub 35. One extension 42 of the lever 40 is positioned alongside the barrel 37 of the syringe where it can be engaged and moved by the fingers of the surgeon. The opposite extension 43 of lever 40 is positioned to engage and move one of the forceps blades 31 to close the blades for grasping the anterior wall 24 of the lens capsule 25 as described above.

The combination syringe/forceps instrument 30 permits the surgeon to inject viscoelastic or fluid into the anterior chamber 23 of the eye during the capsulotomy to replace fluid expressed from that chamber to maintain the shape of the eye.

What is claimed is:

1. A combination of capsulotomy forceps for cataract removal and a syringe for supplying fluid to the forceps, said forceps being characterized by comprising a pair of blades having distal ends, the distal ends of said blades having sharp cystotome tips projecting downwardly therefrom, said tips having a sharpness which enables them to penetrate the anterior wall of a lens capsule, said blades each having a first portion adjacent its distal end extending generally horizontally away from the cystotome tip thereon to a proximal end, said blades each having a second portion joined to the proximal end of said first portion and extending outwardly and upwardly from the proximal end of said first portion at an acute angle with respect to said first portion, at least one of said blades having a fluid flow passage therein and an outlet therefrom in its first portion, and means for imparting relative movement between said blades to bring at least the cystotome tips thereon into contact with each other, said blades being mounted on said syringe with the interior of the syringe in communication with the passage in said one blade.

2. The combination as set forth in claim 1, wherein the means for imparting relative movement between said blades includes a lever carried by said syringe.

* * * * *